(12) United States Patent
Yoda

(10) Patent No.: US 9,247,881 B2
(45) Date of Patent: Feb. 2, 2016

(54) MEASUREMENT APPARATUS, MOVEMENT CONTROL METHOD, AND PROGRAM

(75) Inventor: Haruo Yoda, Nishitama-gun (JP)

(73) Assignee: Canon Kabushiki Kaisha, Tokyo (JP)

( * ) Notice: Subject to any disclaimer, the term of this patent is extended or adjusted under 35 U.S.C. 154(b) by 341 days.

(21) Appl. No.: 13/516,639

(22) PCT Filed: Dec. 10, 2010

(86) PCT No.: PCT/JP2010/072731
§ 371 (c)(1),
(2), (4) Date: Jun. 15, 2012

(87) PCT Pub. No.: WO2011/074656
PCT Pub. Date: Jun. 23, 2011

(65) Prior Publication Data
US 2012/0257472 A1    Oct. 11, 2012

(30) Foreign Application Priority Data

Dec. 18, 2009 (JP) .................................. 2009-288458

(51) Int. Cl.
*A61B 5/00* (2006.01)
*G01S 15/89* (2006.01)
*A61B 8/00* (2006.01)

(52) U.S. Cl.
CPC ............. *A61B 5/0059* (2013.01); *A61B 5/0095* (2013.01); *A61B 8/42* (2013.01); *A61B 8/54* (2013.01); *G01S 15/89* (2013.01)

(58) Field of Classification Search
USPC ............................................... 367/7, 97, 95
See application file for complete search history.

(56) References Cited

U.S. PATENT DOCUMENTS

| 5,713,356 | A | * | 2/1998 | Kruger | 600/407 |
| 5,852,232 | A | * | 12/1998 | Samsavar et al. | 73/105 |
| 6,292,682 | B1 | * | 9/2001 | Kruger | 600/407 |

(Continued)

FOREIGN PATENT DOCUMENTS

| CN | 1846628 A | 10/2006 |
| JP | 2001507952 A | 6/2001 |

(Continued)

OTHER PUBLICATIONS

Kwang et al., "Noninvasive Photoacoustic Imaging of the Thoracic Cavity and the Kidney in Small and Large Animals" American Association of Physicists in Medicine: Medical Physics, Oct. 2008, pp. 4524-4529, vol. 35, No. 10.

(Continued)

*Primary Examiner* — James Hulka
(74) *Attorney, Agent, or Firm* — Canon USA Inc. IP Division

(57) ABSTRACT

Generally, as the time for mechanical scanning of an acoustic wave receiver increases, the load on an examinee also increases. The present invention provides the calculation of a target speed at which an acoustic wave receiver is caused to move for the measurement of an acoustic wave, using data of an emission period of pulsed light and data of an interval between target measurement positions in a subject being examined. In addition, the acoustic wave receiver is caused to move so as to reach an initial target measurement position at the target speed at a time when initial pulsed light for measuring an acoustic wave is emitted. After the target speed has been reached, the acoustic wave receiver is caused to move at a uniform speed which is equal to the target speed.

9 Claims, 10 Drawing Sheets

(56) References Cited

U.S. PATENT DOCUMENTS

| | | | |
|---|---|---|---|
| 6,490,470 B1* | 12/2002 | Kruger | 600/407 |
| 6,633,774 B2* | 10/2003 | Kruger | 600/407 |
| 2002/0193678 A1* | 12/2002 | Kruger | 600/407 |
| 2003/0036751 A1* | 2/2003 | Anderson et al. | 606/9 |
| 2004/0207409 A1* | 10/2004 | Ariav et al. | 324/642 |
| 2005/0004458 A1* | 1/2005 | Kanayama et al. | 600/437 |
| 2007/0187632 A1* | 8/2007 | Igarashi | 250/559.36 |
| 2008/0033679 A1* | 2/2008 | Yamada et al. | 702/95 |
| 2008/0058783 A1* | 3/2008 | Altshuler et al. | 606/9 |
| 2009/0138215 A1 | 5/2009 | Wang et al. | |
| 2009/0214440 A1* | 8/2009 | Bohme et al. | 424/9.37 |
| 2011/0098550 A1* | 4/2011 | Yoda | 600/407 |

FOREIGN PATENT DOCUMENTS

| | | |
|---|---|---|
| JP | 2005-021380 A | 1/2005 |
| JP | 2008-514264 A | 5/2008 |
| JP | 2008-142329 A | 6/2008 |
| WO | 2008101019 A2 | 8/2008 |
| WO | 2009/154244 A1 | 12/2009 |

OTHER PUBLICATIONS

Ma et al.,"Continuous Acquisition Scanner for Whole-Body Multispectral Optoacoustic Tomography" Proc. of SPIE 7564 Jan. 2010, pp. 756429-1-756429-6, vol. 7564.

* cited by examiner

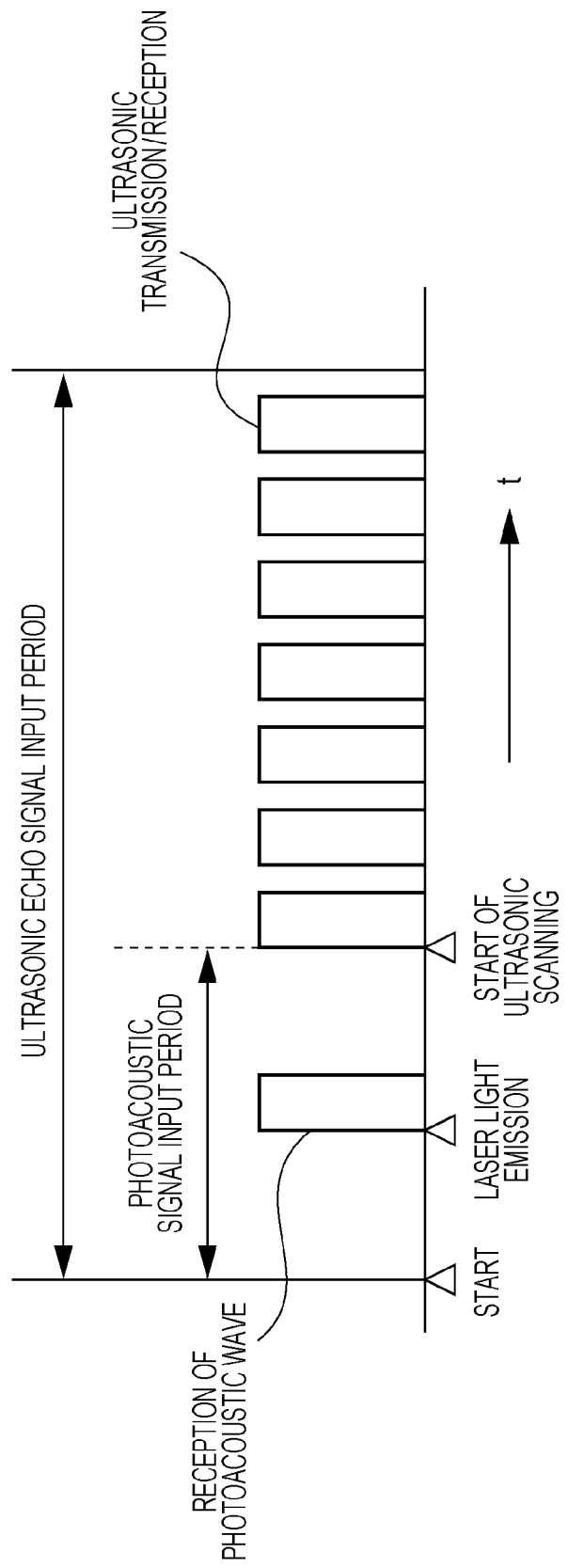

MEASUREMENT APPARATUS, MOVEMENT CONTROL METHOD, AND PROGRAM

TECHNICAL FIELD

The present invention relates to a measurement apparatus that receives, using an acoustic wave receiver, an acoustic wave produced from a subject being examined or imaged, which is irradiated with light, and that generates image data, a movement control method for controlling movement of the acoustic wave receiver, and a program therefor.

BACKGROUND ART

Photoacoustic tomography (PAT) is an imaging technology that uses light, in which an acoustic wave produced by irradiating a subject being examined or imaged with pulsed laser light to thermally expand an object being measured in the subject is received and is converted into an image. PAT allows imaging of the in-vivo distribution of hemoglobin, glucose, or the like of which the absorption band lies in the wavelength of the pulsed laser light to be radiated. PTL 1 describes a method for creating a three-dimensional image of a large examination region using PAT, in which acoustic waves are received at a plurality of positions by a mechanically moving acoustic wave receiver while being sequentially positioned.

One of effective imaging methods for the internal structures of a relatively large subject being examined or imaged, such as a breast, using PAT is to, as disclosed in PTL 1, mechanically scan the surface of the subject with an acoustic wave receiver composed of electroacoustic transducers arranged in a one-dimensional or two-dimensional array. It is desirable that the time required for such mechanical scanning be as short as possible in terms of reduced load on the examinee.

CITATION LIST

Patent Literature

PTL 1 PCT Japanese Translation Patent Publication No. 2001-507952

SUMMARY OF INVENTION

The present invention provides a measurement apparatus capable of causing an acoustic wave receiver to move for a short period of time, and a method for controlling movement of the acoustic wave receiver.

In an aspect of the present invention, a measurement apparatus includes an acoustic wave receiver configured to receive an acoustic wave produced by irradiating a subject being examined with pulsed light and to convert the acoustic wave into an electrical signal, and a movement control unit configured to cause the acoustic wave receiver to move relatively to the subject being examined. The movement control unit calculates a target speed at which the acoustic wave receiver is caused to move for measurement of an acoustic wave, using data of an emission period of the pulsed light and data of an interval between target measurement positions in the subject being examined. The movement control unit causes the acoustic wave receiver to move so as to reach an initial target measurement position at the target speed at a time when initial pulsed light for measuring an acoustic wave is emitted. After the target speed has been reached, the movement control unit causes the acoustic wave receiver to move at a uniform speed which is equal to the target speed.

In another aspect of the present invention, a movement control method for causing an acoustic wave receiver to move relatively to a subject being examined, the acoustic wave receiver being configured to receive an acoustic wave produced by irradiating the subject being examined with pulsed light and to convert the acoustic wave into an electrical signal. The movement control method includes a step of calculating a target speed at which the acoustic wave receiver is caused to move to measure an acoustic wave, using data of an emission period of the pulsed light and data of an interval between target measurement positions in the subject being examined; a first moving step of causing the acoustic wave receiver to move so as to reach an initial target measurement position at the target speed at a time when initial pulsed light for measuring an acoustic wave is emitted; and a second moving step of, after the target speed has been reached, causing the acoustic wave receiver to perform uniform speed movement at the target speed.

According to the present invention, it is possible to cause an acoustic wave receiver to move for a short period of time, resulting in reduced load on an examinee.

BRIEF DESCRIPTION OF DRAWINGS

FIG. 14 is a receiving time chart when an acoustic wave and a reflected acoustic wave are simultaneously obtained.

DESCRIPTION OF EMBODIMENTS

One of the most effective methods to reduce a movement time when an acoustic wave receiver is mechanically moved is to receive acoustic waves while moving the acoustic wave receiver at a uniform speed. Uniform speed movement of the acoustic wave receiver enables a reduction in the time required for start and stop operations at each reception position (target measurement position) of the acoustic wave receiver. In this case, the radiation time of laser light is as short as 10 nsec to 20 nsec, and the time required to receive an acoustic wave is also as short as approximately 50 μsec to 100 μsec. Therefore, even if an acoustic wave is received by a moving receiver, there may be no problem with the quality of a received signal.

Here, a specific method for moving an acoustic wave receiver at a uniform speed may be to constantly monitor the position of the acoustic wave receiver that is moving at a uniform speed and to emit laser light each time the acoustic wave receiver reaches a target measurement position. However, there is a limitation that a high-power pulse laser apparatus suitable for PAT constantly emit light in a certain period to provide a stable amount of light emission. Therefore, it is difficult to control the light emission period of laser light or control the light emission start time in accordance with the movement of the acoustic wave receiver. Accordingly, an effective method to receive acoustic waves while moving an acoustic wave receiver at a uniform speed is to move the acoustic wave receiver in accordance with the light emission period of laser light. However, even such a method of movement may require some technique to reach a target measurement position in accordance with the emission of laser light. In the following embodiments, a specific movement control apparatus and control method for implementing uniform-speed movement will be described.

The term "acoustic wave", as used herein, includes what is called a sound wave, an ultrasonic wave, and a photoacoustic wave, and refers to an elastic wave produced inside a subject being examined or imaged that is irradiated with light (electromagnetic wave) such as near infrared radiation.

First Embodiment

Figure 1:
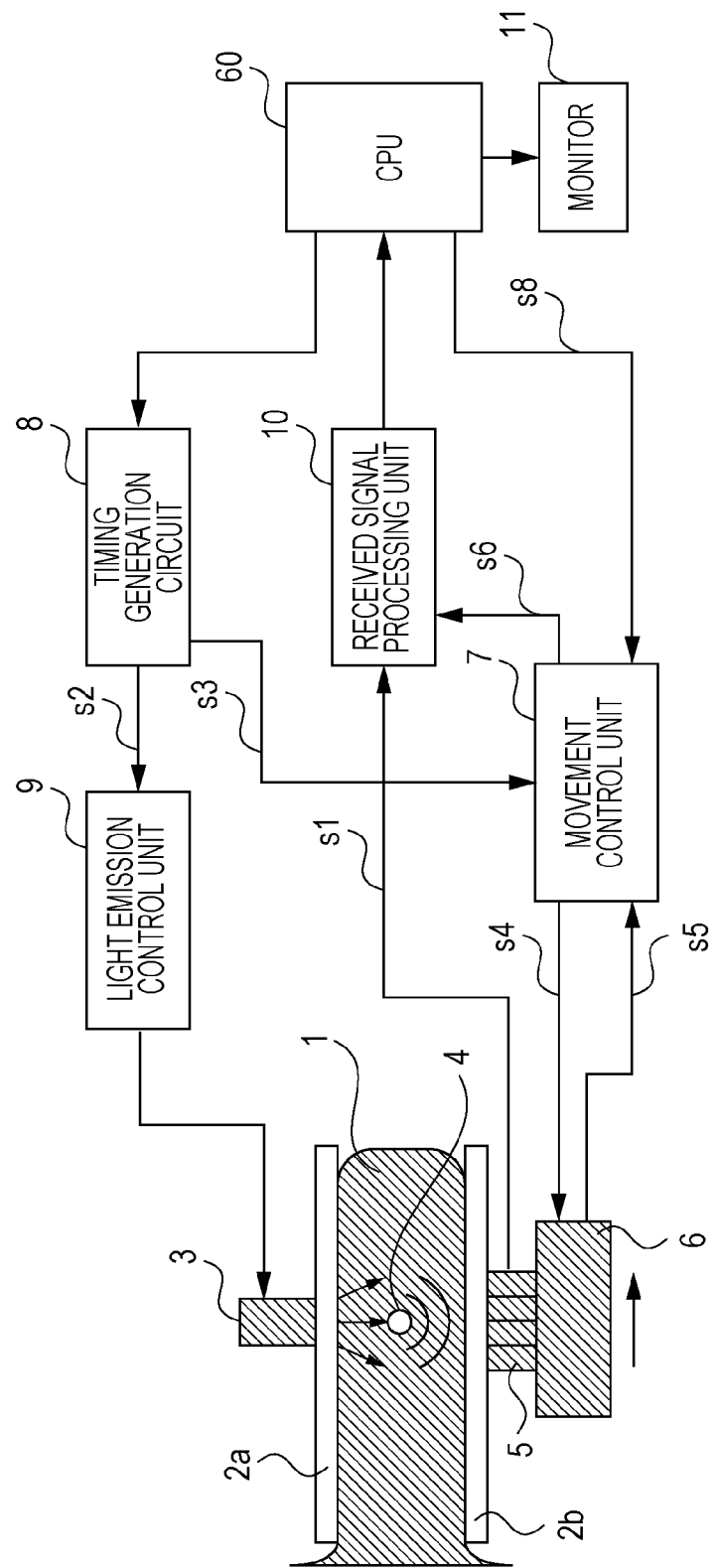
FIG. 1 is a schematic diagram illustrating an overall configuration of a measurement apparatus according to the present invention.

FIG. 1 illustrates an overall configuration of a measurement apparatus according to an embodiment of the present invention. In this embodiment, a subject being examined or imaged 1 (hereinafter referred to as the "subject 1") may be fixed by press plates 2a and 2b. Pulsed laser light generated from a light source 3 is radiated onto the subject 1 through the press plate 2a and is absorbed into an object to be measured 4 (hereinafter referred to as the "measurement object 4") inside the subject 1. An acoustic wave is produced from the measurement object 4 (which may be a light absorbing material such as new blood vessels), and is received by an acoustic wave receiver 5 placed along the outer surface of the press plate 2b. The acoustic wave receiver 5 converts the received acoustic wave into an electrical signal ("received signal s1"), and outputs the received signal s1 to a received signal processing unit 10. The received signal s1 is digitally converted by the received signal processing unit 10, and a resulting signal is sent to a central processing unit (CPU) 60. The acoustic wave receiver 5 is mounted on a stage 6, and is allowed to move along the surface of the press plate 2b by using the stage 6. The stage 6 is controlled to move in accordance with a drive signal s4 output from a movement control unit 7. In other words, the movement of the acoustic wave receiver 5 is controlled by the movement control unit 7.

The light source 3 emits pulsed laser light in accordance with a pulse signal transmitted from a light emission control unit 9. The pulse signal transmitted from the light emission control unit 9 is generated based on a light emission timing instruction signal s2 output from a timing generation circuit 8. The timing generation circuit 8 also outputs a light emission synchronization control signal s3 to the movement control unit 7 in synchronization with the light emission timing instruction signal s2 to be supplied to the light emission control unit 9.

In order to measure an acoustic wave, the CPU 60 transmits one or a plurality of pieces of target measurement position data s8 to the movement control unit 7 to activate the movement control unit 7. The movement control unit 7 generates the drive signal s4 based on the target measurement position data s8 transferred in advance from the CPU 60 and the light emission synchronization control signal s3. The stage 6 is controlled by the drive signal s4, and the acoustic wave receiver 5 mounted on the stage 6 is moved at a uniform speed so that the acoustic wave receiver 5 can pass through each target measurement position at the corresponding light emission time of pulsed laser light. A position signal s5 is output from the stage 6 to the movement control unit 7.

The received signal processing unit 10 is activated by an activation signal s6 output from the movement control unit 7 at the time when the acoustic wave receiver 5 mounted on the stage 6 passes through the initial target measurement position. The received signal processing unit 10 digitally converts the received signal s1, and stores the resulting signal. The digitally converted received signal (digital received signal) is transmitted to the CPU 60. The CPU 60 integrates digital received signals at the individual target measurement positions, and generates two-dimensional or three-dimensional image data of a measurement range on the basis of an integrated digital signal. The generated image data is transmitted to a monitor 11 serving as a display unit, as necessary, and is displayed as an image. In this manner, the acoustic wave receiver 5 can be caused to move relatively to the subject 1 to receive an acoustic wave, and information about the inside of the subject 1 can be obtained as a two-dimensional or three-dimensional image on the basis of a received signal.

In the present invention, the acoustic wave receiver 5 includes a plurality of transducers configured to receive an acoustic wave and convert the acoustic wave into an electrical signal. Each of the transducers may be implemented using any transducer capable of receiving an acoustic wave and converting the acoustic wave into an electrical signal, such as a transducer that utilizes a piezoelectric phenomenon, a transducer that utilizes optical resonance, or a transducer that utilizes a change in capacitance. Further, a plurality of transducers that receive acoustic waves are arranged in a one-dimensional or two-dimensional array, thus allowing acoustic waves to be simultaneously received at a plurality of locations, leading to a reduction in receiving time. In addition, the influence of oscillation or the like of the subject 1 can be reduced. A material for acoustic matching, such as a gel, may be applied between the acoustic wave receiver 5 and the subject 1 to provide acoustic matching.

The light source 3 is designed to emit light with a specific wavelength that is absorbed into a specific component (for example, hemoglobin) among in-vivo components. The light source 3 includes at least one pulse light source capable of generating a light pulse of 5 nsec to 50 nsec. As provided in this embodiment, a high-power laser may be used as the light source 3. However, any source other than a laser, such as a light-emitting diode, may be used. The laser may be any of various lasers such as a solid laser, a gas laser, a dye laser, and a semiconductor laser. Further, light may be emitted from the acoustic wave receiver 5 side, or may be emitted from the side opposite to the acoustic wave receiver 5. Alternatively, the subject 1 may be irradiated with light from both sides thereof. Furthermore, light emitted from a light source may also be directed to the subject 1 using an optical device such as a mirror that reflects light or a lens that condenses light or that enlarges or changes the shape of the image of an object, and may be radiated onto the subject 1. Light may be scattered with a lens to increase the area of the region irradiated with light to some extent. In addition, a portion of the subject 1 irradiated with light may be made movable over the subject 1. In other words, the light emitted from the light source 3 may be made movable over the subject 1. Making the light movable allows a wider area to be irradiated with light. A portion of the subject 1 irradiated with light (light impinging on the subject 1) may be made movable in synchronization with the movement of the acoustic wave receiver 5. A portion of the subject 1 irradiated with light may be made movable using a movable mirror or the like, by mechanically moving the light source 3, or using any other suitable method.

In this embodiment, furthermore, the subject 1 is fixed using the press plates 2a and 2b. However, instead of a pressing mechanism, a shape maintaining member configured to maintain constant the shape of the measurement object 4 of the subject 1 may be used. The shape maintaining member may be a flat plate or a bowl-shaped member provided between the subject 1 and the acoustic wave receiver 5. The shape maintaining member may be implemented by press plates, as in this embodiment, thus allowing light to reach deep inside the subject 1. The material of the shape maintaining member may be selected from those having acoustic impedance similar to that of the subject 1 to efficiently receive acoustic waves. If the subject 1 is a breast or the like, a shape maintaining member made of polymethylpentene may be used. If the shape maintaining member is a flat plate, the thinner the shape maintaining member, the better in terms of the attenuation or the like of acoustic waves. However, the thickness of the shape maintaining member is increased to the extent that its shape does not deform. The thickness may be typically approximately 5 mm to 10 mm. Further, a gap between the shape maintaining member and the subject 1 may be filled with an acoustic gel having substantially the same acoustic impedance as the shape maintaining member (for example, if the subject 1 is a breast, $1.35 \times 10^6$ kg/m$^2$·s) or a liquid such as water (not illustrated) to eliminate the gap.

Figure 2:
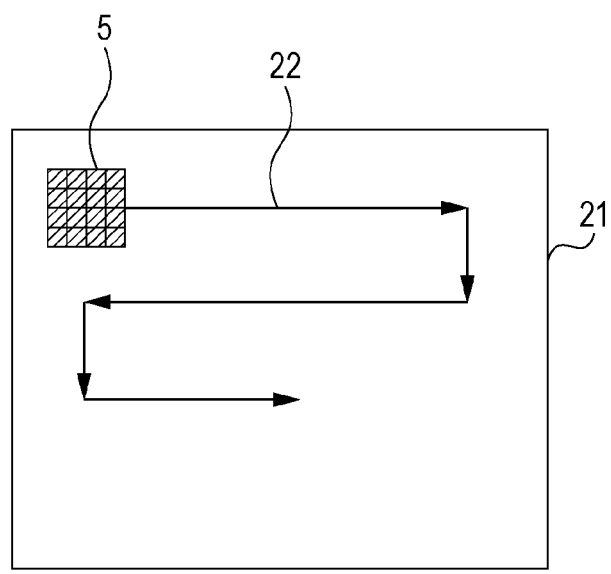
FIG. 2 is a schematic diagram illustrating a path along which an acoustic wave receiver is moved.

FIG. 2 is a diagram illustrating an example of mechanical scanning of the acoustic wave receiver 5 over a surface 21 of the press plate 2b (hereinafter referred to as the "press plate surface 21"). The acoustic wave receiver 5 includes a plurality of transducers arranged in a two-dimensional array. The acoustic wave receiver 5 receives an acoustic wave at each target measurement position while moving at a uniform speed in the transverse direction (one of transducer array directions) along a path 22 illustrated in FIG. 2 over the press plate surface 21. After the completion of reception at the end in the transverse direction, the acoustic wave receiver 5 moves in the longitudinal direction (the direction perpendicular to the above one direction). Then, the acoustic wave receiver 5 receives an acoustic wave at each target measurement position while moving at a uniform speed in the transverse direction again. This allows reception of acoustic waves with high-speed scanning over the entirety of a measurement region on the press plate surface 21.

Figure 3:
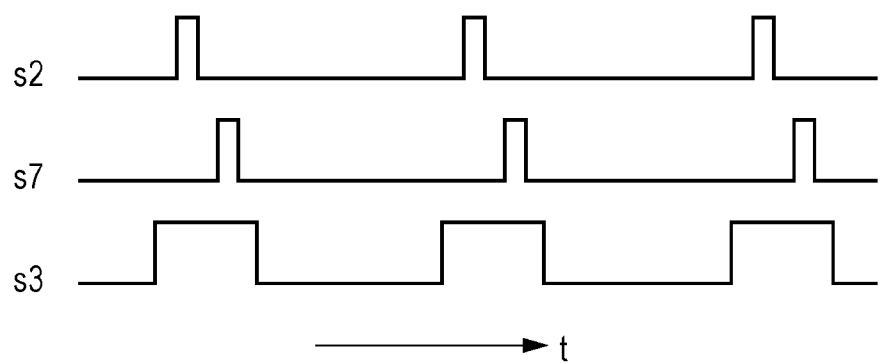
FIG. 3 is a schematic diagram illustrating an example of the waveform of a light emission timing instruction signal, a light emission signal, and a light emission synchronization control signal.

FIG. 3 illustrates a specific waveform of a light emission synchronization control signal s3 suitably used in an embodiment of the present invention. In FIG. 3, s2 represents an example of a light emission timing instruction signal, which may be generally a pulse train signal of approximately 10 Hz for continuous emission of high-power laser pulses suitably used in the embodiment. When the light emission timing instruction signal s2 is input to the light emission control unit 9, as indicated by a light emission signal s7, laser pulses are periodically emitted with a delay of approximately 100 ns to 500 ns. The period of light emission is as short as approximately 10 ns to 20 ns, and there is a limitation that light emission be driven in a certain period of approximately 10 Hz in order to provide a substantially equivalent intensity for every emission of laser light. As illustrated in FIG. 3, the light emission synchronization control signal s3 may be a pulse train signal that rises slightly earlier (by, for example, approximately 10 µs) than the light emission timing instruction signal s2 and that has a time width sufficient for the movement control unit 7 to receive. In this case, the target measurement position data s8 set by the CPU 60 is also corrected so as to indicate a slightly preceding position (a position preceding by, for example, approximately 1 µm) because the light emission synchronization control signal s3 is made to rise slightly early. Thus, even if the received signal processing unit 10 starts a received signal process such as analog-to-digital (A/D) conversion upon detection of the movement control unit 7 that has passed through a target measurement position, a received signal of an acoustic wave immediately after emission of laser light can be processed.

Figure 4:
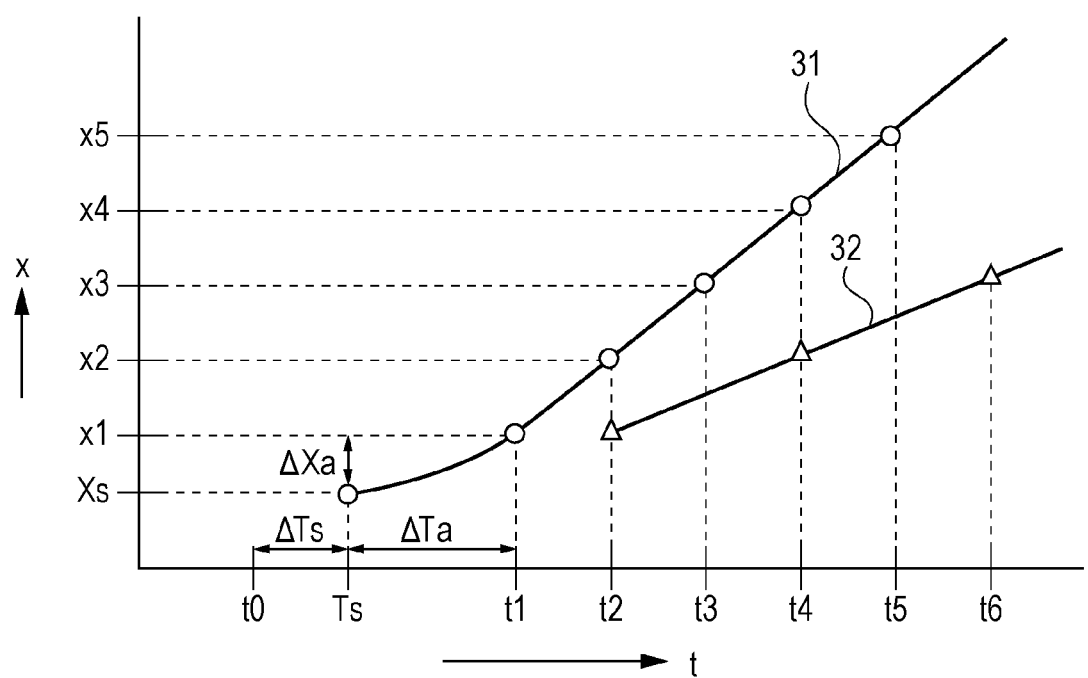
FIG. 4 is a schematic diagram illustrating the operation of the acoustic wave receiver.

FIG. 4 is a schematic diagram illustrating the operation of the stage 6 (that is, the operation of the acoustic wave receiver 5). In FIG. 4, the abscissa represents time, where t1, t2, t3, . . . denote laser light emission times with equal time intervals. The ordinate represents stage position, where x1, x2, x3, . . . denote target measurement positions at equal intervals. The stage 6 may be made to pass through the target measurement positions x1, x2, x3, . . . at the laser light emission times t1, t2, t3, . . . by moving the stage 6 at a uniform speed along a measurement line 31 illustrated in FIG. 4. In this case, a target speed Vmes of the acoustic wave receiver 5 for the measurement of an acoustic wave may be a value obtained by dividing the interval between target measurement positions by the time interval between the laser light emission times. If the target speed Vmes exceeds a maximum speed that allows the stage 6 to move, as indicated by a measurement line 32, every other laser light emission may be used. Here, the time required until the stage 6 that has stopped operating is accelerated with a constant acceleration A and reaches the target speed Vmes is represented by ΔTa, and a moving distance is represented by ΔXa. If ΔTa and ΔXa are known, the stage 6 can be moved along the measurement line 31 by sequentially executing the following steps:

1. The stage 6 is moved to a start position Xs ahead of x1 by the distance ΔXa, and is stopped.
2. Movement with a uniform acceleration that is equal to the acceleration A is started at a time Ts that is ΔTa ahead of the initial measurement time t1 at which an acoustic wave is to be measured (first moving step).
3. At time t1, the operation is switched to uniform speed movement at the target speed Vmes (second moving step).

Here, since ΔTa may be known, acceleration of the stage 6 may be started at the time Ts that is delayed by ΔTs=(t1−t0−ΔTa) with respect to a reference time t0 of laser light emission. In this case, the delay time ΔTs needs to have a positive value. However, the light emission times t1, t2, . . . may be advanced or delayed by an integer multiple of the light emission period. Therefore, the light emission time for which the delay time ΔTs=(t1−t0−ΔTa) has a minimum positive value may be determined as t1.

Figure 5:
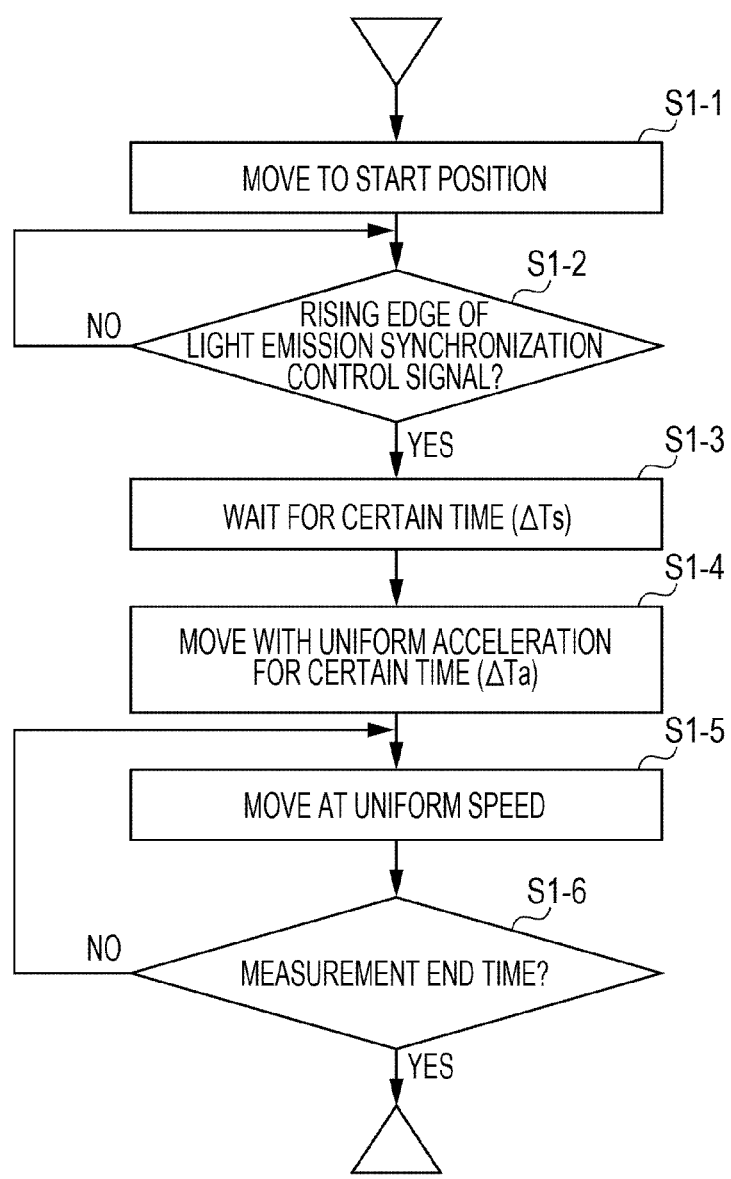
FIG. 5 is a flowchart illustrating a control procedure of a movement control unit.

FIG. 5 is a flowchart illustrating the above operation, which will be described in detail below. The movement control unit 7 monitors the light emission synchronization control signal s3. When a rising edge of the light emission synchronization control signal s3 is detected, after waiting for the given time ΔTs, the stage 6 starts moving with a uniform acceleration that is equal to the certain acceleration A. When the target speed Vmes is reached after the lapse of the given time ΔTa, the stage 6 then moves at a uniform speed that is equal to the target speed Vmes. After the stage 6 passes through the last target measurement position, the movement of the stage 6 ends.

Figure 6:
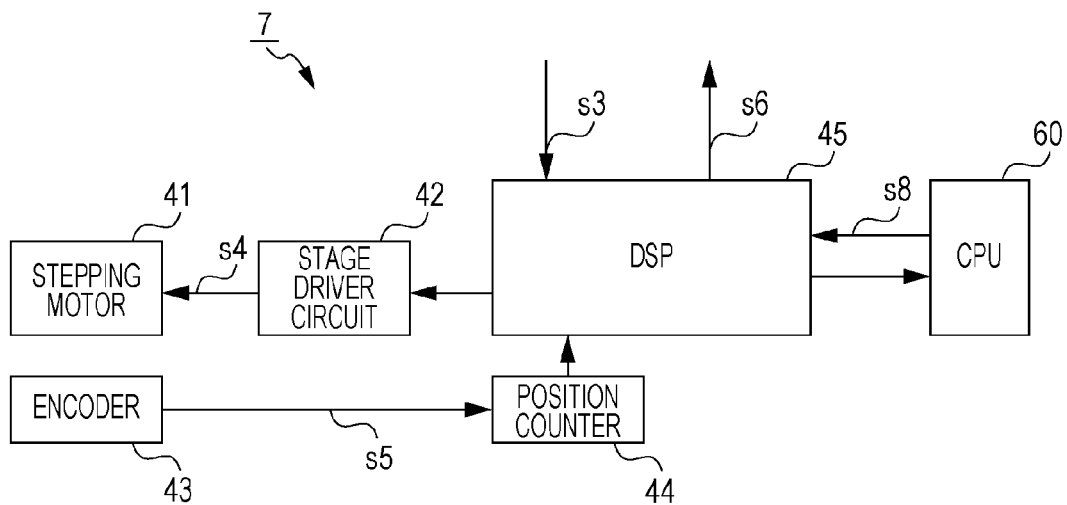
FIG. 6 is a schematic diagram illustrating the configuration of the movement control unit.

FIG. 6 illustrates a specific example configuration of the movement control unit 7. In the example configuration, the stage 6 is configured to be driven by a stepping motor 41, and a pulse signal used for the driving operation is calculated and generated at a required time by a built-in calculator digital signal processor (DSP) 45. Specifically, when the DSP 45 outputs a forward pulse signal, the forward pulse signal is converted into a drive signal s4 by a stage driver circuit 42, and the stepping motor 41 rotates in the forward direction by the rotation angle corresponding to one pulse. When the DSP 45 outputs a negative pulse signal, the stepping motor 41 rotates in the negative direction by the rotation angle corresponding to one pulse. The position of the stage 6 driven by the stepping motor 41 (that is, the position of the acoustic wave receiver 5) can be read by counting, using a position counter 44, the pulse s5 output from an encoder 43 serving as a position detection unit provided in the stage 6.

The process of the DSP 45 will now be specifically described. When the target measurement position data s8 is transferred from the CPU 60, first, the DSP 45 calculates the operation schedule of the stage 6 in accordance with the following calculation steps:

1. The target speed Vmes is calculated.

If the interval between target measurement positions is represented by Xp and the emission period (emission time interval) of pulsed laser light is represented by T1, the target speed Vmes can be calculated by $$Vmes=Xp/T1.$$

When the target speed Vmes exceeds a maximum speed that allows the stage 6 to move, measurement is performed once for k emissions of laser light, and the target speed Vmes may be changed to one k-th. However, for the ease of description, it is assumed here that the target speed Vmes does not exceed the maximum speed.

2. The time ΔTa required for acceleration up to the target speed Vmes, and the distance ΔXa are calculated.

The time ΔTa and the distance ΔXa are calculated using the equations below, assuming that the maximum allowable acceleration of the stage 6 is represented by Am:

$$\Delta Ta=Vmes/Am$$

$$\Delta Xa=(\tfrac{1}{2})*Am*(\Delta Ta)^2$$

The acceleration Am may not necessarily be the maximum allowable acceleration. However, setting the acceleration Am to the maximum allowable acceleration can minimize the measurement time.

3. The start position Xs of the stage 6 and the delay time ΔTs are calculated.

If the initial target measurement position is represented by x1, the start position Xs of the stage 6 can be calculated by $$Xs=x1-\Delta Xa.$$

Further, the delay time ΔTs can be calculated as a minimum value for which ΔTs+ΔTa is set as an integer multiple of the laser light emission period T1. If the reference time of single laser light emission is represented by t0 and the calculated delay time ΔTs is used, the measurement times (that is, light emission times of laser light) t1, t2, t3, . . . can be calculated by:

$$t1=t0+\Delta Ts+\Delta Ta$$

$$t2=t1+T1$$

$$t3=t1+2*T1$$

$$t4=t1+3*T1$$

All the position parameters and time parameters required for the movement of the stage 6 can be calculated using the above calculations. Therefore, the scheduling of the specific operation in accordance with the flowchart of FIG. 5 described above can be performed.

Next, a specific process of the DSP 45 during measurement will be described with reference to the flowchart of FIG. 5. Upon receipt of a start instruction from the CPU 60, first, the DSP 45 moves the stage 6 to the start position Xs, and waits (S1-1). Then, the DSP 45 monitors a rising edge of the light emission synchronization control signal s3 (S1-2). When the light emission synchronization control signal s3 rises, the DSP 45 sets the rising time of the light emission synchronization control signal s3 as the reference time t0, and waits for the delay time ΔTs (S1-3). Then, the stage 6 is caused to start moving with a uniform acceleration that is equal to the acceleration Am (S1-4).

If the current time is represented by t and the amount of movement of the stage 6 per pulse of the stepping motor 41 is represented by dX, the speed V of the stage 6 at time t in the acceleration time zone (t0+ΔTs<t<t1) is given by $$V=Am*(t-t0-\Delta Ts).$$

In order to cause the stage 6 to move at the speed V, the DSP 45 calculates a time interval dT given by $$dT=dX/(Am*(t-t0-\Delta Ts)),$$

and outputs one pulse to the stage driver circuit 42 each time the time interval dT has elapsed. Since the time interval dT decreases as time passes, the speed of the stage 6 is accelerated accordingly. At time t1 at which an acoustic wave is first measured, the speed of the stage 6 matches the target speed Vmes.

If the time t has reached the measurement time t1, the DSP 45 switches the movement of the stage 6 to uniform speed movement at the target speed Vmes (S1-5). In order to cause the stage 6 to move at a uniform speed that is equal to the target speed Vmes, the DSP 45 calculates a time interval dT given by $$dT=dX/Vmes,$$

and outputs one pulse to the stage driver circuit 42 each time the time interval dT has elapsed. After that, the DSP 45 determines whether or not the measurement end time has been reached (S1-6). If the end time has been reached (that is, if the stage 6 has passed through the last target measurement position), the movement of the stage 6 ends.

Figure 7:
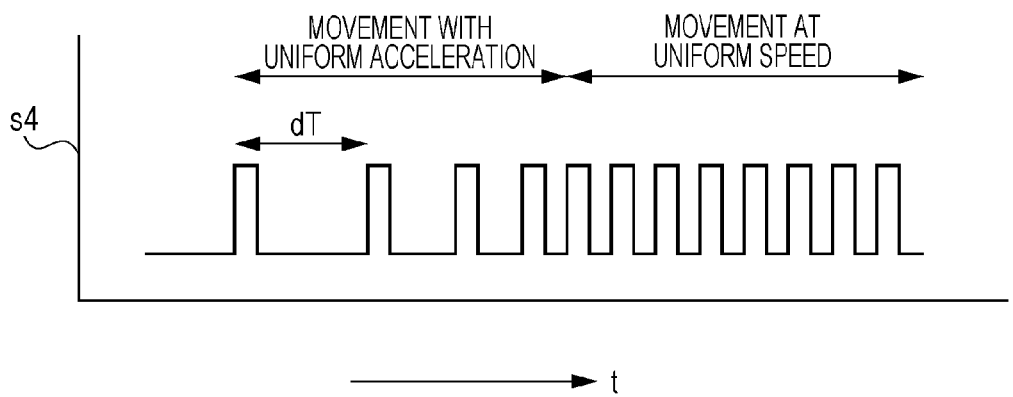
FIG. 7 is a schematic diagram illustrating a drive pulse train when a stepping motor is used.

FIG. 7 illustrates the timing of pulses generated by the DSP 45. Thus, the acoustic wave receiver 5 can pass through all the target measurement positions at the laser light emission times at a uniform speed, and the flowchart of FIG. 5 can be implemented in a specific manner.

Here, the receiving position of an acoustic wave may match a target measurement position with an accuracy of at least approximately 5% to 10% of the size of the transducers. Matching with the above accuracy can reduce phase variation of received signals when, as in a third embodiment described below, acoustic waves generated from the same position in the subject 1 are received, and can improve the resolution of image data. If the size of the electroacoustic transducers is 2 mm, matching with an accuracy of approximately ±50 μm to ±100 μm may be desirable.

Further, the light emission synchronization control signal s3 according to the present invention can be easily generated using the timing generation circuit 8 that generates the light emission timing instruction signal s2 in the manner described above. Further, since laser light is emitted regularly in a constant period, the light emission synchronization control signal s3 can also be generated by directly detecting the emission of laser light if the period is known. Furthermore, if the light emission period of laser light is known, a light emission time may be detected once using some method, and a light emission synchronization control signal having a constant period can be generated with reference to the light emission time within the timing generation circuit 8. The above configurations may be modifications of an embodiment of the present invention, and may also fall within the scope of the present invention.

Second Embodiment

With the first embodiment described above, the DSP can control the stage 6 to pass through all the target measurement positions at the laser light emission times at a uniform speed. In a second embodiment, the movement control unit 7 monitors the light emission synchronization control signal s3, and reads the value of the position counter 44 at a rising edge of the light emission synchronization control signal s3. If there is an error from the target measurement position at this time, the moving speed of the stage 6, that is, the time interval of pulse outputs of the drive signal s4, is adjusted so as to eliminate or reduce the error by the next laser light emission time. With this control, if a slight calculation error occurs in the calculation of the time interval dT of generation of pulses or the amount of movement of the stage 6 per pulse using the DSP 45, a non-negligible position error due to the accumulation of errors can be prevented from occurring between the position of the stage 6 at the emission time of laser light and a target measurement position. Further, in case of open control without detection of the position of the stepping motor 41, an error caused by a mechanical distortion or the like can also be prevented from being added to the position error.

Figure 8:
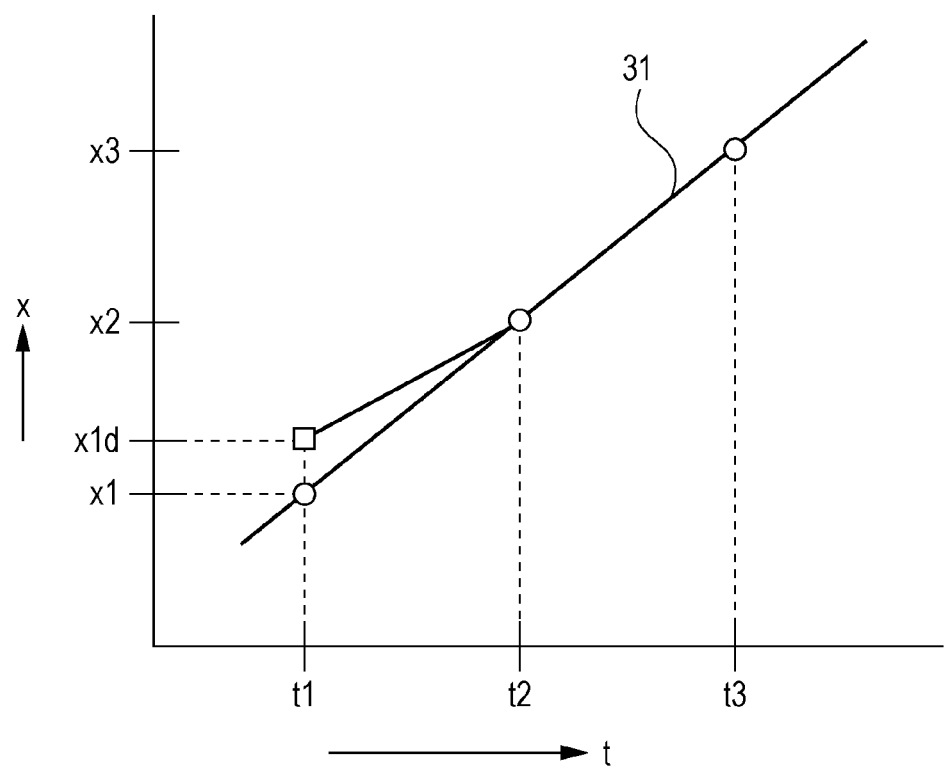
FIG. 8 is a schematic diagram illustrating the operation of the acoustic wave receiver for correcting a position shift.
Figure 9:
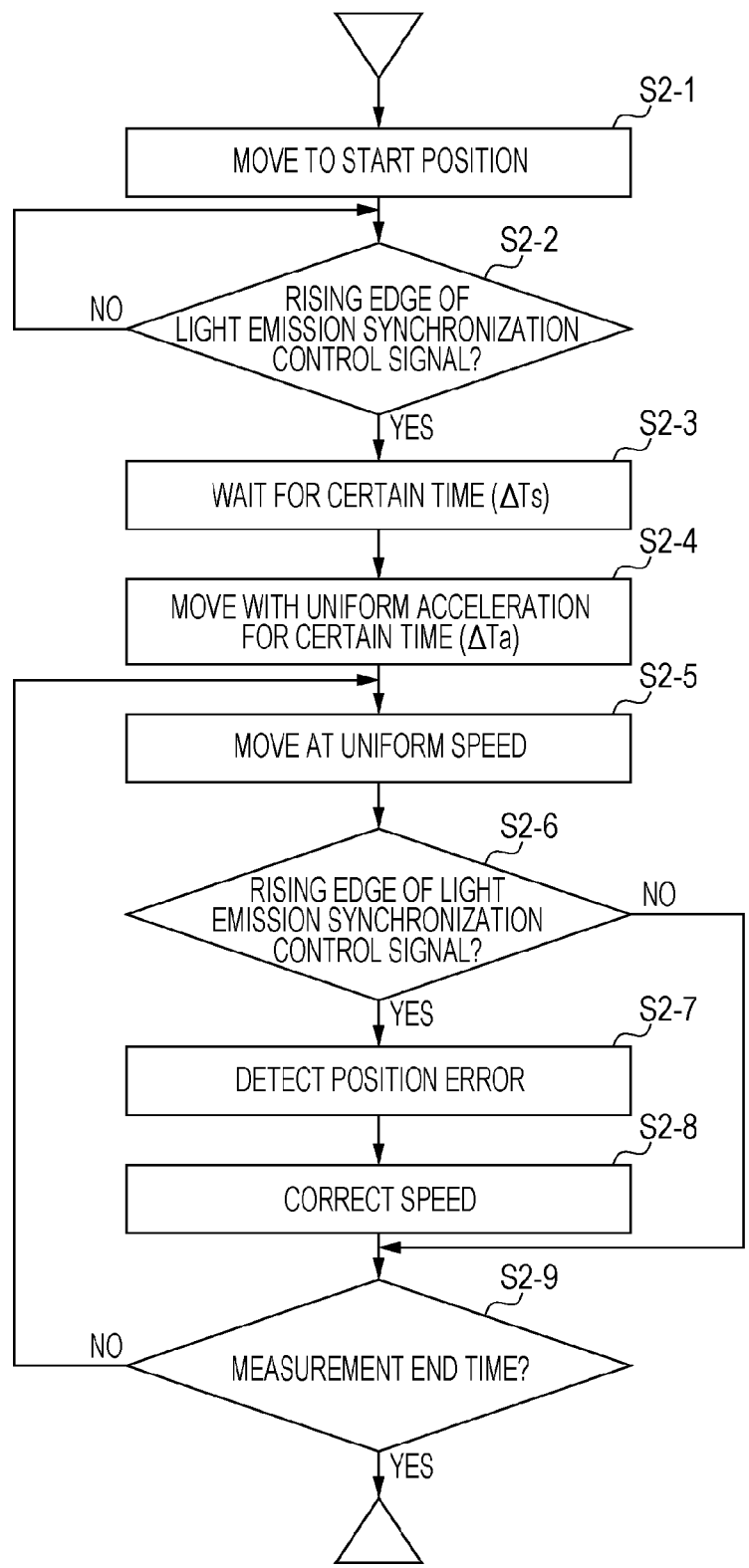
FIG. 9 is a flowchart illustrating a control procedure of the movement control unit for correcting a position shift.

FIG. 8 is a schematic diagram illustrating the movement of the stage 6 in this embodiment. If the value of the position counter 44 indicates a position x1$d$ at the laser light emission time t1, the stage 6 is moved so that the target speed Vmes until the next laser light emission time t2 has been reached is changed to $$Vmes=(x2-x1d)/(t2-t1)$$

so as to reduce the difference from a target measurement position x1 by the next laser light emission time t2. FIG. 9 is a flowchart illustrating the operation of the stage 6 in this case. The processing of steps S2-1 to S2-5 is the same as or similar to the procedure of steps S1-1 to S1-5 in the first embodiment. In step S2-6, the current position x1$d$ is measured at the time when a rising edge of the light emission synchronization control signal s3 is detected. Then, a position error is detected (S2-7), and the speed of the stage 6 is corrected (S2-8). In step S2-9, similarly to step S1-6, it is determined whether or not the measurement end time has been reached. If the end time has been reached (that is, if the stage 6 has passed through the last target measurement position), the movement of the stage 6 ends. With this control, speed correction can be performed so that a position error can be reduced in accordance with the above equation at each rising time of the light emission synchronization control signal s3. According to this embodiment, a position error is directly measured and is corrected at a laser light emission time. Thus, a position error can be corrected using a simple method regardless of the cause of the position error, and accurate movement control can be performed without using an expensive apparatus.

An embodiment in which a stepping motor is used has been described. However, a direct current (DC) servo motor or the like may also be used.

Third Embodiment

Figure 10:
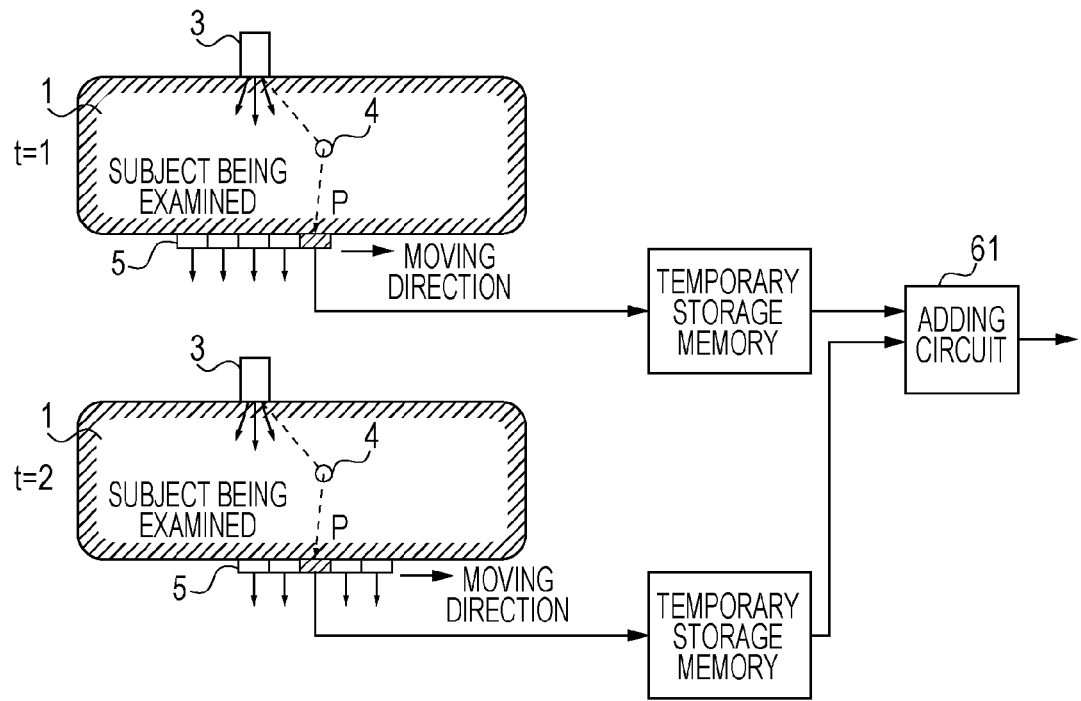
FIG. 10 is a schematic diagram illustrating a case where coverage areas of the acoustic wave receiver overlap.

In a third embodiment, there is an overlapping region where coverage areas of an acoustic wave receiver at adjacent target measurement positions (a first target measurement position and a second target measurement position) overlap. FIG. 10 is a schematic diagram illustrating the position of an acoustic wave receiver 5 at each measurement time. In this embodiment, as illustrated in FIG. 10, an adding circuit that calculates the sum of electrical signals output from transducers located at a position P in the overlapping region is used. A specific description will now be given.

The acoustic wave receiver 5 passes through the first target measurement position at laser light emission time t=1, and passes through the second target measurement position at laser light emission time t=2. The adding circuit 61 averages a received signal obtained by a transducer that has received an acoustic wave at the position P at time t=1, which is stored in a temporary storage memory, and a received signal obtained by a transducer that has received an acoustic wave at the same position, that is, the position P, at the second target measurement position. This enables the generation of a received signal with less noise. In this case, the received signals to be summed are digitally converted signals. Further, the sum of the received signals obtained by the adding circuit 61 is transmitted to the CPU 60 illustrated in FIG. 1, and is converted into image data through image reconstruction processing such as phasing addition.

Overlapping of coverage areas of the acoustic wave receiver 5 in the longitudinal direction in addition to the transverse direction can further reduce the noise of a received signal. The use of the first or second embodiment may enable accurate reception of an acoustic wave at a target measurement position even while moving the stage 6 at a uniform speed, thus facilitating the implementation of averaging as in the third embodiment and ensuring the reception of a high-speed photoacoustic signal with less noise.

Fourth Embodiment

In a fourth embodiment, an acoustic wave receiver 5 configured to receive an acoustic wave produced by radiation of light, and an acoustic wave transmitter and receiver 51 configured to transmit an acoustic wave (typically, an ultrasonic wave) and to receive a reflected acoustic wave reflected from an object being measured are integrated. In the following description, an acoustic wave produced by radiation of light is referred to as a "photoacoustic wave", and a reflected acoustic wave obtained by reflecting and returning an acoustic wave transmitted from the acoustic wave transmitter and receiver 51 from an object being measured is referred to as an "ultrasonic echo".

Figure 11:
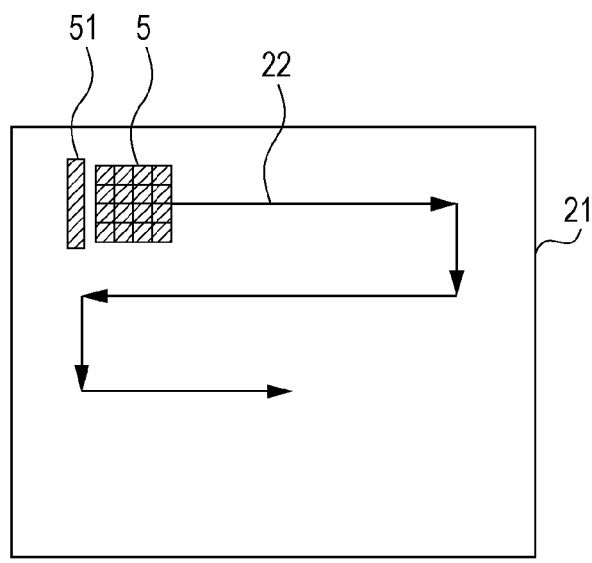
FIG. 11 is a schematic diagram illustrating integral movement of an acoustic wave receiver and an acoustic wave transmitter and receiver.
Figure 12:
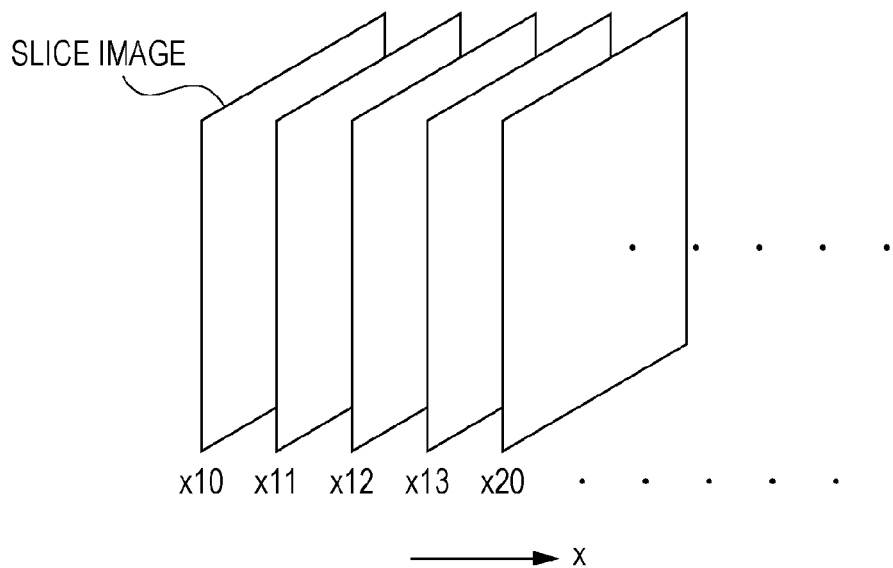
FIG. 12 is a schematic diagram illustrating slice images generated using an electrical signal from the acoustic wave transmitter and receiver.

As illustrated in FIG. 11, in this embodiment, the acoustic wave receiver 5 configured to receive a photoacoustic wave and the acoustic wave transmitter and receiver 51 configured to receive an ultrasonic echo are integrally placed on a stage, and are caused to move over a press plate surface 21. The acoustic wave transmitter and receiver 51 may be composed of transducers arranged in a one-dimensional array, and may be capable of creating slice in-plane ultrasonic echo images using ultrasonic beam scanning in the one-dimensional array direction. Therefore, three-dimensional image data of the inside of the subject being examined or imaged can be easily created by moving the acoustic wave transmitter and receiver 51 for ultrasonic echoes at a uniform speed and, as illustrated in FIG. 12, repeatedly creating slice images at individual positions x10, x11, x12, . . . in the moving direction.

Figure 13:
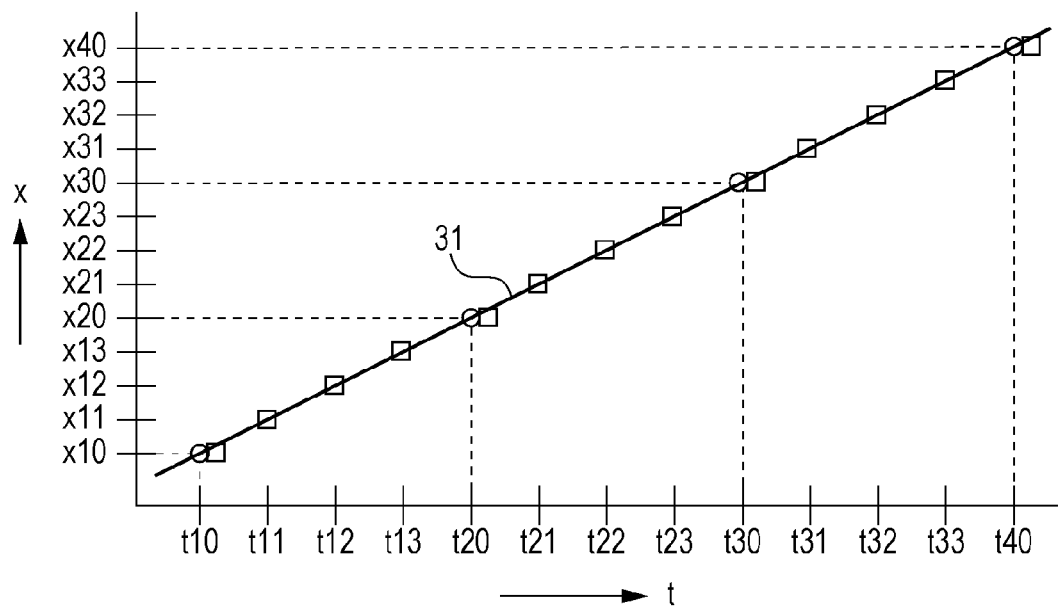
FIG. 13 is a schematic diagram illustrating an operation when the acoustic wave receiver and the integrated acoustic wave transmitter and receiver are integrated.

When ultrasonic echo image data is created, slice images are created at equal intervals with a smaller pitch than the intervals during which photoacoustic waves are received in order to increase resolution in the moving direction of the stage. FIG. 13 illustrates an embodiment of the above measurement operation. An ultrasonic transmission/reception operation for creating individual pieces of slice image data may be started at time points indicated by circular marks on a photoacoustic signal measurement line 31 and at time points indicated by rectangular marks located at the positions equally divided between the circular marks.

The time points indicated by the circular marks also represent the measurement points of photoacoustic waves. However, as illustrated in FIG. 14, a photoacoustic signal input period for receiving a photoacoustic wave is provided during a period from the start of the ultrasonic transmission/reception operation to the start of transmission and reception of an ultrasonic beam, and emission of laser light and reception of a photoacoustic wave are performed during the input period. This enables correct signals to be received without interference between a photoacoustic wave and an ultrasonic echo.

Even at the time of the start of the ultrasonic transmission/reception operation without performing the emission of laser light, the operation of receiving an ultrasonic echo may be performed at the same timing as that with performing the emission of laser light. In this case, slice images can be created at completely equal intervals in terms of time and position. The creation of an individual slice image requires multiple transmissions and receptions of ultrasonic beams. Since the photoacoustic signal input period is shorter than the time required for the transmissions and receptions, even making the echo signal input periods of all the slice planes equal has substantially no influence on the overall throughput.

In the present invention, a stage passes through target measurement positions at the laser light emission times at a uniform speed, and therefore, the start time or start position of ultrasonic transmission/reception can be calculated as the operation schedule so as not to cause interference between photoacoustic signals and ultrasonic echo signals. Therefore, a DSP is configured to start the ultrasonic transmission/reception operation each time the calculated start time or start position has been reached, thus enabling a photoacoustic wave and an ultrasonic echo to be obtained even in a method in which a stage is moved at a uniform speed.

The present invention may also be implemented by executing the following processing. Software (program) implementing the functions of the first to fourth embodiments described above may be supplied to a system or an apparatus via a network or various storage media, and a computer (or any other suitable device such as a CPU or a microprocessing unit (MPU)) of the system or the apparatus may read and execute the program.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2009-288458, filed Dec. 18, 2009, which is hereby incorporated by reference herein in its entirety.

REFERENCE SIGNS LIST

1 Subject being examined or imaged
2a Press plate
2b Press plate
3 Light source
4 Object being measured
5 Acoustic wave receiver
6 Stage
7 Movement control unit
8 Timing generation circuit
9 Light emission control unit
10 Received signal processing unit
11 Monitor
s1 Received signal
s2 Light emission timing instruction signal
s3 Light emission synchronization control signal
s4 Drive signal
s5 Position signal
s6 Activation signal
s7 Light emission signal
21 Press plate surface
22 Path (along which an acoustic wave receiver moves on a press plate surface)
31 Measurement line
32 Measurement line
41 Stepping motor
42 Stage driver circuit
43 Encoder
44 Position counter
45 DSP
51 Acoustic wave transmitter and receiver
60 CPU

The invention claimed is:

1. An apparatus comprising:
a light source configured to emit pulsed light;
an acoustic wave receiver configured to receive an acoustic wave produced by irradiating a subject being examined with the pulsed light and to convert the acoustic wave into an electrical signal;
a positional information detection unit configured to detect information on a position of the acoustic wave receiver; and a movement control unit configured to cause the acoustic wave receiver to move relatively to the subject being examined, a moving speed of the acoustic wave receiver being set based on the information on the position of the acoustic wave receiver,
wherein the acoustic wave receiver includes a plurality of conversion elements configured to convert an acoustic wave into an electrical signal, and
wherein the movement control unit is configured to cause the acoustic wave receiver to move so that a position where one of the conversion elements is positioned when one pulsed light is emitted coincides with a position where another of the conversion elements is positioned when another pulsed light is emitted.

2. The apparatus according to claim 1, further comprising an adding circuit configured to add electrical signals into which acoustic waves received by the one of the conversion elements are converted and electrical signals into which acoustic waves received by the another of the conversion elements are converted.

3. The apparatus according to claim 2, wherein the adding circuit is configured to average the added electrical signals.

4. The apparatus according to claim 1, further comprising a timing generation circuit configured to give an instruction for generation timing to the light source,
wherein the timing generation circuit is configured to output a signal synchronized with the generation timing to the movement control unit.

5. The apparatus according to claim 4, wherein the timing generation circuit is configured to emit pulsed light from the light source with a predetermined period.

6. The apparatus according to claim 4, wherein the movement control unit is configured to cause the acoustic wave receiver to move at a constant speed using the signal synchronized with the generation timing.

7. The apparatus according to claim 1, further comprising an acoustic wave transmitter and receiver configured to transmit an acoustic wave to the subject being examined and to receive a reflected acoustic wave reflected from an object being measured in the subject being examined,
   wherein the movement control unit is configured to cause the acoustic wave receiver and the acoustic wave transmitter and receiver to move integrally.

8. The apparatus according to claim 1, further comprising a received signal processing unit configured to digitally convert the electrical signal obtained through conversion by the acoustic wave receiver,
   wherein the received signal processing unit is configured to generate image data using the electrical signal digitally converted by the received signal processing unit.

9. The apparatus according to claim 1, wherein the movement control unit is configured to adjust the moving speed during a period from a time when the one pulsed light is emitted to a time when the another pulsed light is emitted.

\* \* \* \* \*